United States Patent
Hendriks et al.

(10) Patent No.: US 11,910,995 B2
(45) Date of Patent: Feb. 27, 2024

(54) INSTRUMENT NAVIGATION IN ENDOSCOPIC SURGERY DURING OBSCURED VISION

(71) Applicant: KONINKLIJKE PHILIPS N.V., Eindhoven (NL)

(72) Inventors: Bernardus Hendrikus Wilhelmus Hendriks, Eindhoven (NL); Caifeng Shan, Veldhoven (NL); Marco Lai, Eindhoven (NL); Robert Johannes Frederik Homan, Batenburg (NL); Drazenko Babic, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 46 days.

(21) Appl. No.: 17/629,260

(22) PCT Filed: Jul. 10, 2020

(86) PCT No.: PCT/EP2020/069510
§ 371 (c)(1),
(2) Date: Jan. 21, 2022

(87) PCT Pub. No.: WO2021/013579
PCT Pub. Date: Jan. 28, 2021

(65) Prior Publication Data
US 2022/0240759 A1    Aug. 4, 2022

(30) Foreign Application Priority Data

Jul. 23, 2019  (EP) .................................... 19187857

(51) Int. Cl.
*A61B 1/00*  (2006.01)
*G06T 7/73*  (2017.01)
(Continued)

(52) U.S. Cl.
CPC .. *A61B 1/000096* (2022.02); *A61B 1/000095* (2022.02); *G06T 3/00* (2013.01);
(Continued)

(58) Field of Classification Search
CPC . G06T 1/0007; G06T 2210/41; G06T 19/003; G06T 19/00; G06T 7/0012;
(Continued)

(56) References Cited

U.S. PATENT DOCUMENTS 4,960,422 A    10/1990  Demeester
9,646,423 B1    5/2017  Sun
(Continued)

FOREIGN PATENT DOCUMENTS

JP    2010051531 A    3/2010
WO    2010063240 A1    6/2010

OTHER PUBLICATIONS

International Search Report and Written Opinion of PCT/EP2020/069510, dated Sep. 9, 2020.
(Continued)

*Primary Examiner* — Ming Wu

(57) ABSTRACT

The application relates to the problem of navigating a surgical instrument (at 301, 311) towards a region-of-interest (at 312) in endoscopic surgery when an image (300) provided by the endoscope is obscured at least partly by obscuring matter (at 303), wherein the obscuring matter is a leaking body fluid, debris or smoke caused by ablation. To address this problem, a computer-implemented method is proposed, wherein, upon detecting that the image from the endoscope is at least partly obscured, a second image is determined based on a sequence of historic images and based on the current position and orientation of the endoscope. Furthermore, a virtual image (310) is generated based on the determined second image.

15 Claims, 2 Drawing Sheets

(51) Int. Cl.
*G06T 7/90* (2017.01)
*G06T 3/00* (2006.01)
*G06T 7/00* (2017.01)
*G06T 11/00* (2006.01)

(52) U.S. Cl.
CPC .............. *G06T 7/0016* (2013.01); *G06T 7/73* (2017.01); *G06T 7/90* (2017.01); *G06T 11/00* (2013.01); *G06T 2207/10016* (2013.01); *G06T 2207/10068* (2013.01); *G06T 2207/20212* (2013.01); *G06T 2207/30204* (2013.01); *G06T 2207/30244* (2013.01); *G06T 2210/41* (2013.01)

(58) Field of Classification Search
CPC .......... G06T 7/11; G06T 11/00; G06T 11/006; G06T 15/20; G06T 17/00; G06T 2207/10028; G06T 2207/10121; G06T 2207/30048; G06T 2210/22; G06T 2211/424; G06T 2219/008; G06T 7/30; G06T 7/62

See application file for complete search history.

(56) References Cited

U.S. PATENT DOCUMENTS

| | | | |
|---|---|---|---|
| 9,833,254 B1* | 12/2017 | Barral | ............ A61B 17/320068 |
| 11,638,615 B2* | 5/2023 | Nir | ........................ A61B 34/25 600/102 |
| 2004/0034300 A1 | 2/2004 | Verard | |
| 2009/0182349 A1 | 7/2009 | Poran | |
| 2013/0018255 A1 | 1/2013 | Kitamura | |
| 2015/0313503 A1 | 11/2015 | Seibel | |
| 2015/0374309 A1* | 12/2015 | Farkas | ............... A61B 5/14558 600/407 |
| 2016/0157726 A1 | 6/2016 | Itai | |
| 2016/0249989 A1 | 9/2016 | Devam | |
| 2017/0085762 A1 | 3/2017 | Obara | |
| 2019/0038362 A1* | 2/2019 | Nash | ...................... A61B 34/25 |

OTHER PUBLICATIONS

Elmi-Terander, Adrian et al "Surgical Navigation Technology Based on Augmented Reality and Integrated 3D Intraoperative Imaging", Spine, vol. 41, No. 21, pp. E1303-E1311, 2016.

Lai,. Marco et al "Hand-Eye Camera Calibration with an Optical Tracking System", Proceedings of the 12th International Conf. on Distributed Smart Cameras, ACM, 2018.

Winne, Christian et al "Overlay Visualization in Endosopic ENT Surgery", International Journal Cars, vol. 6, pp. 401-406,2011.

Plantefeve, Rosallie et al "Patient-Specific Biomechanical Modeling for Guidance during Minimally-Invasive Hepatic Surgery", Annals of Biomedical Engineering, vol. 44, No. 1, Jan. 2016, pp. 139-153.

* cited by examiner

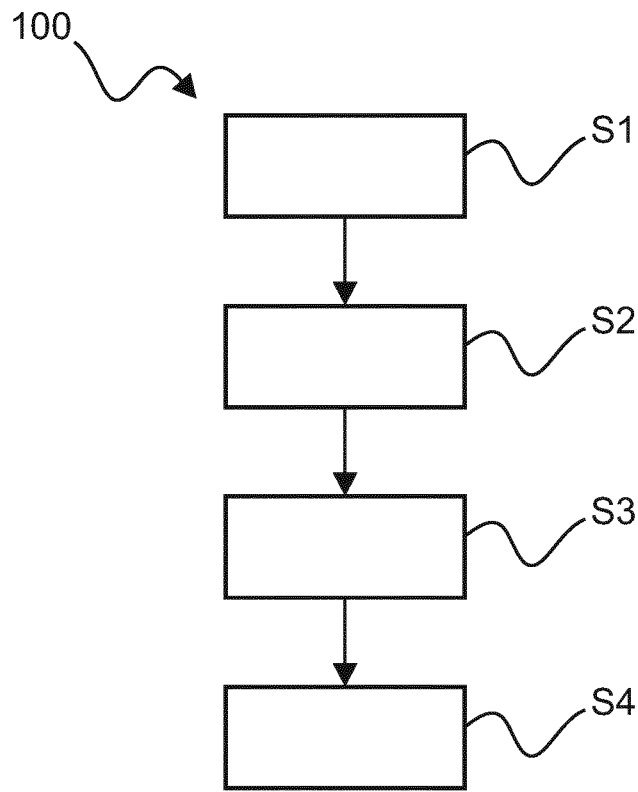
FIG. 1
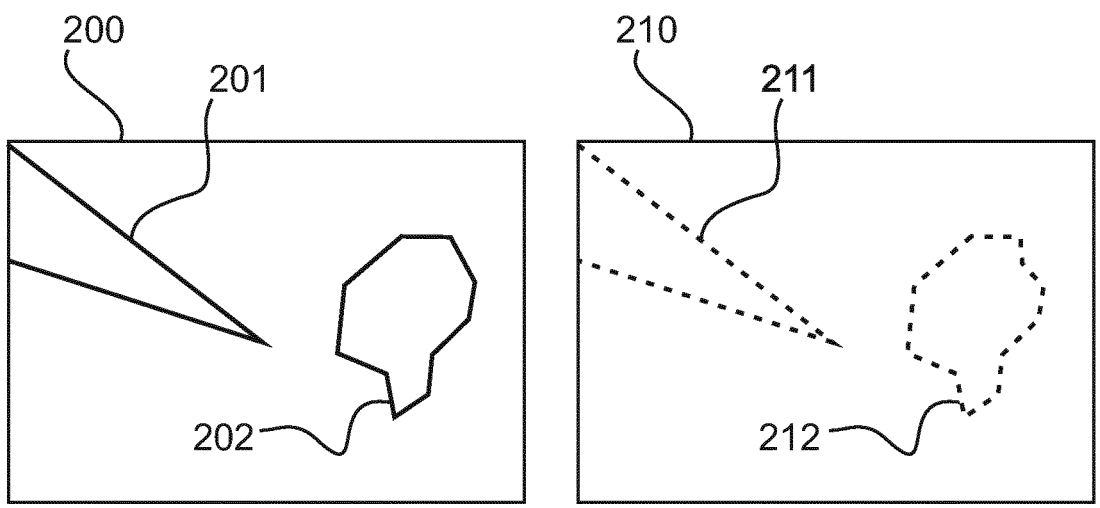
FIG. 2A  FIG. 2B

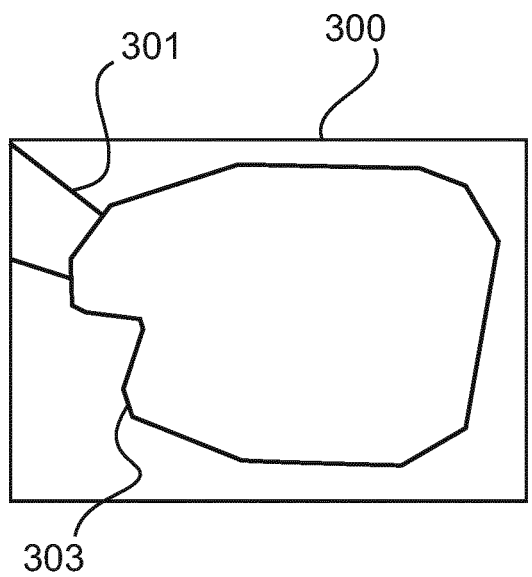
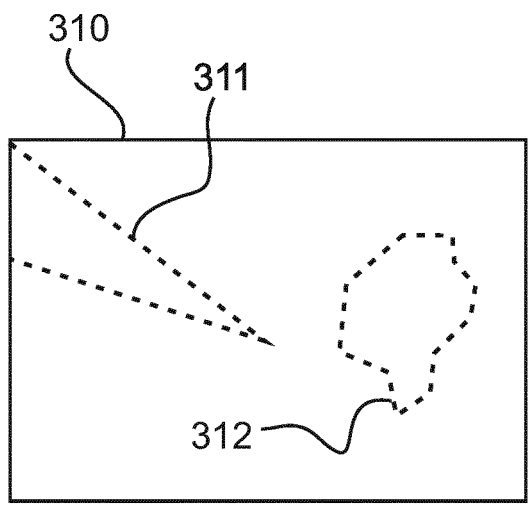
FIG. 3A          FIG. 3B
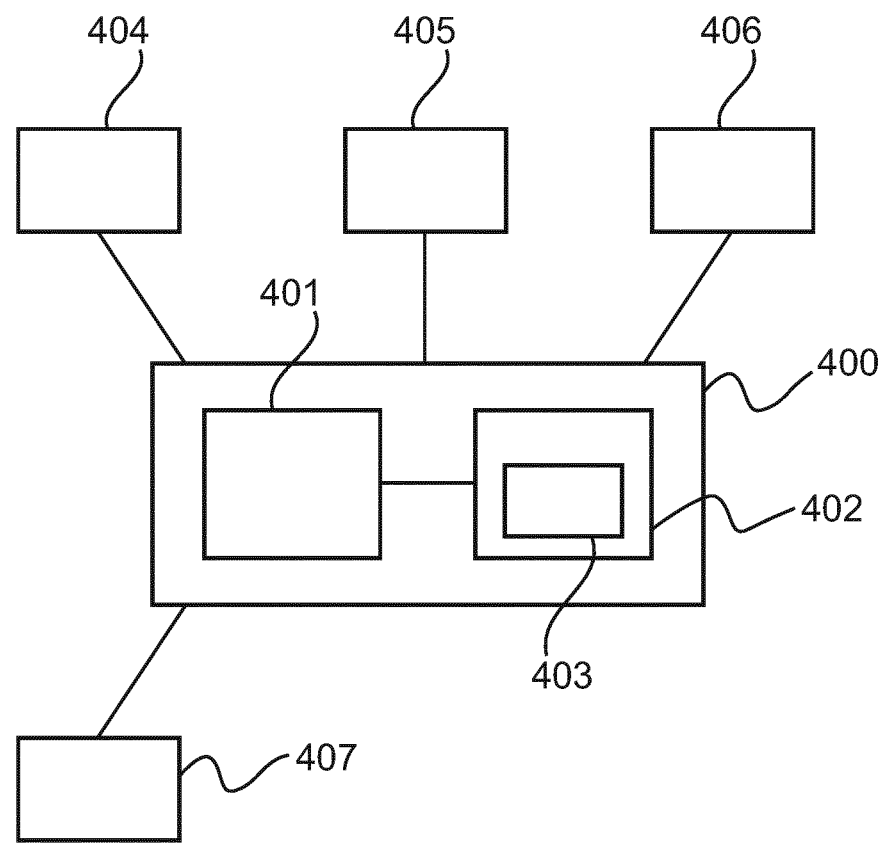
FIG. 4

INSTRUMENT NAVIGATION IN ENDOSCOPIC SURGERY DURING OBSCURED VISION

CROSS-REFERENCE TO PRIOR APPLICATIONS

This application is the U.S. National Phase application under 35 U.S.C. § 371 of International Application No. PCT/EP2020/069510, filed on Jul. 10, 2020, which claims the benefit of European Patent Application No. 19187857.8, filed on Jul. 23, 2019. These applications are hereby incorporated by reference herein.

FIELD OF THE INVENTION

The invention relates to a computer-implemented method for an image-assisted medical application, a data processing system configured to carry out the steps of this method, a computer program comprising instructions to cause the data processing system to execute the method, and a computer-readable medium having stored such computer program.

BACKGROUND OF THE INVENTION

Minimally invasive surgery is often guided by endoscopic vision. The endoscope comprises a miniature camera, preferably a video camera, which may allow viewing the tissue in a body cavity that requires treatment. The vision provided by the endoscope's camera may facilitate navigating an instrument towards a region-of-interest. During the treatment, the vision provided by the camera may be obscured. For example, the vision provided by the camera may be obscured by a leaking body fluid such as a bleeding caused by tissue resection, by debris, or by smoke from ablation.

For example in the case of a bleeding, the leaking blood vessel has to be identified, which is difficult when the endoscopic vision is obscured by the bleeding. The intervention may have to be interrupted until endoscopic vision is cleared. Currently, water flushing near the distal end of the endoscope is applied in order to clear the vision. However, since the bleeding is not stopped, this may not be effective. Thus, the surgical instrument may have to be maneuvered blindly, without knowing its location with respect to the tissue.

US 2015/313503 discloses a method for imaging with one or more endoscopes. The method involves acquiring images with the endoscopes and creating a virtual model from the images.

US 2013/018255 discloses a virtual endoscope image generation unit which receives a three dimensional medical image as an input and generates a virtual endoscope image representing a body cavity in real time.

US 2017/085762 discloses an endoscope system which includes an insertion portion, observation windows and an image processing portion. One observation window is configured to acquire forward visual field images and another observation window is used to acquire lateral visual field images.

US 2016/157726 discloses a method and program that generate a projection image from volume data representing a three-dimensional region including a hollow organ.

SUMMARY OF THE INVENTION

It may be desirable to provide an improved method allowing to increase safety of medical applications and/or treatments. For example, the method may allow to safely navigate surgical instruments during minimally invasive surgery while the image provided by the endoscope is at least partly obscured by a leaking body fluid such as a bleeding, by debris, or by smoke caused by ablation.

This is achieved by the subject matter of the independent claims, wherein further embodiments are incorporated in the dependent claims and the following description. It should be noted that any step, feature or aspect of the computer-implemented method, as described in the following, equally applies to the data processing system configured to carry out the steps of the method, the computer program, and the computer readable medium, as described in the following, and vice versa.

According to the present disclosure, a computer-implemented method and/or medical method for an image-assisted medical application is presented. The method may generally refer to a computer-implemented data processing method. The method comprises the following steps: (i) acquiring a first image of at least one body part of a patient, the first image being captured with an endoscope and being associated with sensor data, the sensor data being indicative of a first position and orientation of the endoscope; (ii) detecting if the first image is at least partly obscured by obscuring matter, such that the first image includes an image of a leaking body fluid, debris or smoke from ablation; (iii) determining, upon detecting that the first image is at least partly obscured, a second image based on a sequence of historic images and based on the first position and orientation of the endoscope, wherein the historic images of the sequence of historic images each have image capturing times earlier than the first image; and (iv) generating a virtual image of the at least one body part based on the determined second image.

The term "detecting if the first image is at least partly obscured by obscuring matter" may be understood as "detecting if the first image includes an image of obscuring matter, which obscuring matter obscures the at least one body part (or a portion thereof)".

The first image may be received from the endoscope or from an intermediate device, which forwards the first image. Alternatively, the first image may be retrieved from a storage medium. The first image visualizes at least one body part of a patient, wherein the patient may be a human or an animal.

The endoscope may be a laparoscope, cystoscope, nephroscope, bronchoscope, arthroscope, or colonoscope. Preferably, the endoscope is a rigid endoscope so that the position and orientation of the camera at the distal end of the endoscope can be inferred from the position and orientation of a visible proximal end of the endoscope. The first position and orientation of the endoscope may be defined as the position and orientation of the endoscopic camera.

The sensor data may have been recorded by a tracking system such as a camera-based tracking system. The camera-based tracking system may comprise one or more cameras, which capture images from one or more positions and orientations. At least a proximal end of the endoscope may be visible in one or more images captured by the camera-based tracking system. The first position and orientation of the endoscope may be determined based on this visualization of the proximal end of the endoscope in one or more camera images, based on information about the shape of the endoscope, based on information about the shape of a marker-plate, which may be attached to the endoscope, and/or based on information about the geometry of the cameras of the tracking system. The position and orientation of the endoscope may be defined with respect to a coordinate system that is stationary relative to the position and orientation of the patient or relative to the position and orientation of an operating table, on which the patient may be lying.

The sensor data may be received from the tracking system or from an intermediate device, which forwards the sensor data. Alternatively, the sensor data may be retrieved from a storage medium. The sensor data may be the raw recorded sensor data, or it may be a processed version thereof. Preferably, the sensor data is recorded by the tracking system at the same time when the endoscope captures the first image. Hence, the first position and orientation of the endoscope determined based on the sensor data may be an estimate of the image capturing position and orientation of the first image. However, the endoscope may not be coupled to the tracking system, so the capturing time of the first image may diverge from the time of recording the sensor data. The difference in time may be negligible as long as the position and orientation of the endoscope does not change significantly in the meantime.

It is detected if the first image is at least partly obscured by obscuring matter, wherein the obscuring matter is a leaking body fluid, debris or smoke caused by ablation. The term 'obscuring matter' is used here and in the following for a leaking body fluid, debris or smoke caused by ablation. The leaking body fluid may be but not limited to a bleeding, bile or gall leaking out of a bile duct or an exudate (pus) of a site of inflammation. Furthermore, for the sake of brevity, an image is referred to herein as being 'obscured' when at least a part of the image is obscured by a leaking body fluid, debris or smoke from ablation. The obscuring matter may obscure a part of the first image, so that the first image may not show for example an instrument and/or a region-of-interest. Thus, due to the obscuring matter, it may be difficult or impossible to securely navigate the instrument towards the region-of-interest based on the first image.

When it is detected that the first image is at least partly obscured, the first position and orientation of the endoscope may be determined based on the sensor data, and a second image may be determined based on the sequence of historic images and based on the first position and orientation of the endoscope. The sequence of historic images may comprise endoscopic images, which have been captured by the endoscope before capturing the first image.

Determining the second image may comprise, for example, retrieving the second image from the sequence of historic images such that a measure for the difference between the first position and orientation of the endoscope and the image capturing position and orientation of the second image is small. Thus, the second image may be identical with one of the historic images from the sequence of historic images. The image capturing position and orientation of the second image may differ from the first position and orientation of the endoscope.

Alternatively, determining the second image may comprise, for example, generating a three-dimensional model of the patient's anatomy from the sequence of two-dimensional historic images. The second image may then be determined based on the three-dimensional model and the first position and orientation of the endoscope. In this case, the second image may differ from all historic images in the sequence of historic images, and its associated image capturing position and orientation may be identical with the first position and orientation of the endoscope.

A virtual image is then generated based on the second image. The virtual image may be equal to the second image. However, the generation of the virtual image may also comprise various transformations of the second image. For example, the second image may be transformed to adjust its associated image capturing position and orientation. Furthermore, the second image may be augmented with a rendering of an instrument. In addition, the second image may be augmented with image data from an X-ray imaging system, a magnetic resonance imaging (MRI) system, a single-photon emission computerized tomography (SPECT) system or an ultrasound device.

The virtual image may not be based on image data of the first image. Hence, even when the first image is obscured by obscuring matter, the virtual image may provide a virtual endoscopic view, which is not obscured by obscuring matter. The method may comprise displaying the virtual image to provide an unobscured view to a user.

In an example, the sensor data is also indicative of a position and orientation of an instrument, and the method further comprises the following steps: Determining a second position and orientation of the instrument based on the sensor data, and augmenting the virtual image with a rendering of the instrument in accordance with the second position and orientation of the instrument and in accordance with an image capturing position and orientation of the virtual image.

The instrument may be any instrument used for minimally invasive surgery, including, but not limited to, forceps, spatulas, retractors, dilators, graspers, sutures, visualizing scopes, cutter instruments such as trocars and rasps, electrosurgical instruments, guiding devices, surgical staplers, needles, catheters and inflation systems.

The sensor data may have been recorded by a tracking system such as a camera-based tracking system. The camera-based tracking system may comprise a plurality of cameras, which capture images from a plurality of positions and orientations. At least a proximal end of the instrument may be visible in one or more images captured by the camera-based tracking system. The second position and orientation of the instrument may be determined based on this visualization of the proximal end of the instrument in one or more camera images, based on information about the shape of the instrument, based on information about the shape of a marker-plate, which may be attached to the instrument, and/or based on information about the geometry of the cameras of the tracking system.

The virtual image may be augmented with a rendering of the instrument in accordance with the second position and orientation of the instrument and in accordance with an image capturing position and orientation of the virtual image, so that the virtual image provides a virtual endoscopic view, which shows the instrument in accordance with its current position and orientation. The instrument may be rendered based on a three-dimensional model of the instrument.

In another example, determining the second image comprises retrieving the second image from the sequence of historic images based on a measure for a difference between the first position and orientation of the endoscope and an image capturing position and orientation of the second image.

The second image may be retrieved from the sequence of historic images such that the measure for the difference between the first position and orientation of the endoscope and the image capturing position and orientation of the second image is small or such that the measure for the difference is minimized over the image capturing positions and orientations of the historic images in the sequence of historic images. The measure for the difference between the first position and orientation of the endoscope and the image capturing position and orientation of the second image may be a function, e.g. a weighted sum, of a measure for the difference between the first position of the endoscope and the image capturing position of the second image and a measure for the difference between the first orientation of the endoscope and the image capturing orientation of the second image.

Additionally or alternatively, the second image may be retrieved from the sequence of historic images based on the difference between the image capturing times of the first and second images. For example, the second image may be retrieved from the sequence of historic images such that a measure for the difference between the first position and orientation of the endoscope and the image capturing position and orientation of the second image is small subject to the constraint that the difference between the image capturing times of the first and second images does not exceed a threshold.

In another example, the determination of the second image is also based on a determination for one or more images if they are at least partly obscured by obscuring matter to ensure that the determined second image is not obscured by obscuring matter.

For example, determining the second image may comprise retrieving the second image from the sequence of historic images based on a measure for a difference between the first position and orientation of the endoscope and an image capturing position and orientation of the second image and based on a determination for one or more images if they are obscured by obscuring matter to ensure that the retrieved second image is not obscured by such matter. The sequence of historic images may comprise obscured and non-obscured historic images, and it may be determined for one or more historic images from the sequence of historic images if they are obscured by obscuring matter to ensure that the retrieved second image is not obscured by such matter. Hence, the obscured historic images may be excluded when retrieving the second image. Alternatively, an image may be included in the sequence of historic images only if it is determined that this image is not obscured by obscuring matter, so the sequence of historic images may comprise only non-obscured historic images.

Alternatively, a three-dimensional model of the patient's anatomy may be generated from the sequence of two-dimensional historic images, and the second image may be determined based on the three-dimensional model and the first position and orientation of the endoscope. The sequence of historic images may comprise obscured and non-obscured historic images, and it may be determined for one or more historic images from the sequence of historic images if they are obscured by obscuring matter to ensure that parts of historic images, which are obscured by such matter, are not taken into account for generating the three-dimensional model, so that also the second image is not obscured by obscuring matter. Alternatively, before including an image in the sequence of historic images, it may be determined if the image is obscured by obscuring matter to ensure that the sequence of historic images comprises only non-obscured historic images.

In another example, generating the virtual image comprises transforming the second image by means of the structure from motion technique, wherein the virtual image corresponds to an image capturing position and orientation equal to the first position and orientation of the endoscope.

The image capturing position and orientation of the second image may diverge from the first position and orientation of the endoscope. The first position and orientation of the endoscope may be equal or close to the current position and orientation of the endoscope. Hence, by transforming the second image such that the virtual image has an image capturing position and orientation equal to the first position and orientation of the endoscope, a virtual image may be generated, which corresponds to the current position and orientation of the endoscope. The second image may be transformed by means of the structure from motion technique or by means of any other image processing technique suitable for adjusting the image capturing position and orientation of the second image.

In another example, the method further comprises displaying an indicator for a difference between the first position and orientation of the endoscope and an image capturing position and orientation of the second image.

When the virtual image has been generated by transforming the second image such that the virtual image has an image capturing position and orientation equal to the first position and orientation of the endoscope, for instance by means of the structure from motion technique, then displaying the indicator for the difference between the first position and orientation of the endoscope and the image capturing position and orientation of the second image may provide an indication for the reliability of the virtual image. Furthermore, displaying the indicator for the difference between the first position and orientation of the endoscope and the image capturing position and orientation of the second image may indicate to a user how to adjust the current position and orientation of the endoscope to reduce the difference between the current position and orientation of the endoscope and the image capturing position and orientation of the second image, thereby increasing the reliability of the virtual image.

Alternatively, when the virtual image has an image capturing position and orientation equal to that of the second image, then the indicator for the difference between the first position and orientation of the endoscope and the image capturing position and orientation of the second image may indicate to the user how to adjust the current position and orientation of the endoscope such that the current position and orientation of the endoscope becomes equal to the image capturing position and orientation of the virtual image.

In another example, the method further comprises displaying the first image from the endoscope and the virtual image next to each other.

The first image may provide an endoscopic view, which may be obscured by obscuring matter, whereas the virtual image may provide a virtual unobscured endoscopic view. Displaying the first and virtual images next to each other may allow the user to compare these images and to assess the reliability of the virtual image. The first and virtual images may be displayed separately, for example next to each other, on top of each other, or otherwise shifted relative to each other. The first and virtual images may be displayed on the same screen or on different screens.

In another example, the historic images of the sequence of historic images are endoscopic images.

For example, when it is detected that the first image is not obscured by obscuring matter, this image may be included in the sequence of historic images after detecting that it is not obscured. On the other hand, when it is detected that the first image is at least partly obscured by obscuring matter, this image may be included in the sequence of historic images after generating the virtual image.

The sequence of historic images may comprise images, which are obscured by obscuring matter, as well as images, which are not obscured by such matter. The sequence of historic images may be stored in a database. Hence, the method may comprise storing the first image in the database. Furthermore, the method may comprise storing the first position and orientation of the endoscope in association with the first image. Furthermore, the method may comprise storing the image capturing time of the first image in association with the first image. Furthermore, the method may comprise storing an indicator in association with the first image, wherein the indicator indicates if the first image is obscured by obscuring matter. Furthermore, the method may comprise storing another indicator in association with the first image, wherein the another indicator indicates if the first image comprises a visualization of an instrument.

Alternatively, the sequence of historic images may comprise only unobscured images. Thus, the method may comprise storing the first image in the database upon detecting that the first image is not obscured by obscuring matter.

In another example, detecting if the first image is obscured by obscuring matter comprises detecting if the first image is obscured by a bleeding, wherein detecting if the first image is obscured by a bleeding comprises determining a size of a red section in the first image and/or determining a contrast in at least a part of the first image.

Detecting if the first image is obscured by a bleeding may comprise detecting if the size of a red section increased over time and/or by detecting if the image contrast in at least a part of the image decreased over time. This may be accomplished by comparing the first image with an earlier image having an image capturing time earlier than the first image. For example, the earlier image may be a historic image from the sequence of historic images.

Hence, detecting if the first image is obscured by a bleeding may comprise detecting if the size of a red section in the earlier image is smaller than the size of a red section in the first image. Additionally or alternatively, detecting if the first image is obscured by a bleeding may comprise detecting if the image contrast in at least a part of the earlier image is higher than the image contrast in at least a part of the first image.

More specifically, detecting if the size of a red section in the earlier image is smaller than the size of a red section in the first image may comprise determining a red section in the earlier image, determining a measure for the size of the red section in the earlier image, determining a red section in the first image, determining a measure for the size of the red section in the first image, and determining if the difference between the measures for the sizes of the red sections in the first and earlier images exceeds a threshold.

Further, detecting if the image contrast in at least a part of the earlier image is higher than the image contrast in at least a part of the first image may comprise determining a part of the earlier image, determining a measure for the image contrast in the part of the earlier image, determining a part of the first image, determining a measure for the image contrast in the part of the first image, and determining if the difference between the measures for the image contrast in the earlier and first images exceeds a threshold.

The detection if the first image is obscured by a bleeding may be performed by means of a neural network, which may be trained using standard machine learning techniques. One input parameter of the neural network may be based on the measure for the size of the red section in the earlier image and/or based on the measure for the size of the red section in the first image. Another input parameter of the neural network may be based on the measure for the image contrast in the part of the earlier image and/or based on the measure for the image contrast in the part of the first image. Another input parameter of the neural network may be based on the image capturing time of the earlier image and/or based on the image capturing time of the first image. Another input parameter of the neural network may be based on the image capturing position and orientation of the earlier image and/or based on the image capturing position and orientation of the first image. For example, one input parameter of the neural network may be based on the projection of the vector from the image capturing position of the earlier image to the image capturing position of the first image onto the direction of the image capturing orientation of the earlier image.

More generally, detecting if the first image is obscured by a leaking body fluid or by smoke caused by ablation may comprise detecting if the image contrast in at least a part of the image decreased over time. Again, this may be accomplished by comparing the first image with an earlier image such as a historic image from the sequence of historic images. Hence, detecting if the first image is obscured by a leaking body fluid or by smoke from ablation may comprise detecting if the image contrast in at least a part of the earlier image is higher than the image contrast in at least a part of the first image.

The detection if the first image is obscured by a leaking body fluid or by smoke from ablation may again be performed by means of a neural network. One input parameter of the neural network may be based on a measure for the image contrast in a part of the earlier image and/or based on a measure for the image contrast in a part of the first image. Another input parameter of the neural network may be based on the image capturing time of the earlier image and/or based on the image capturing time of the first image. Another input parameter of the neural network may be based on the image capturing position and orientation of the earlier image and/or based on the image capturing position and orientation of the first image. For example, one input parameter of the neural network may be based on the projection of the vector from the image capturing position of the earlier image to the image capturing position of the first image onto the direction of the image capturing orientation of the earlier image.

In another example, the method further comprises determining a position of an origin of obscuring matter based on the sequence of historic images, and/or indicating a position of an origin of obscuring matter in the virtual image.

Determining a position of an origin of obscuring matter may comprise searching for a first historic image in the sequence of historic images, wherein the first historic image is not obscured by obscuring matter, whereas the next-in-time historic image in the sequence of historic images is obscured the obscuring matter. The position of the obscuring matter in the next-in-time historic image may then provide an indication for the position of the origin of the obscuring matter.

When the obscuring matter is a leaking body fluid such as a bleeding, then indicating the position of the origin of the leaking body fluid in the virtual image may allow a user to navigate an instrument towards the origin of the leaking body fluid in order to stop the leakage of the body fluid. Similarly, when the obscuring matter is debris or smoke from ablation, then indicating the position of the origin of the debris or the smoke from ablation in the virtual image may inform a user where certain treatments may be required.

In another example, the sensor data is received from a camera-based tracking system, and/or the first position and orientation of the endoscope is determined based on a marker plate attached to the endoscope.

The camera-based tracking system may comprise one or more cameras, which may capture images from one or more positions and orientations. At least a proximal end of the endoscope may be visible in one or more images captured by the camera-based tracking system. The first position and orientation of the endoscope may be determined based on this visualization of the proximal end of the endoscope in one or more camera images and based on information about the geometry of the tracking cameras. Additionally, information about the shape of the endoscope may be utilized for determining the position and orientation of the endoscope.

When a marker plate is attached to the endoscope, the position and orientation of the endoscope may be determined based on a single image from a single camera. However, a camera-based tracking system comprising a plurality of cameras still provides benefits as compared to a single camera system. For example, in the case of a plurality of cameras, it is more likely that the endoscope is visible in at least one of the camera images as compared to a single camera system, so the determination of the first position and orientation of the endoscope is more reliable. Additionally or alternatively, the plurality of cameras and the associated image processing algorithms may be configured to provide a statistically more accurate determination of the position and orientation of the endoscope as compared to a single camera system.

In another example, the method further comprises acquiring a third image, the third image being captured with an X-ray imaging system, a computed tomography (CT) system, a single-photon emission computerized tomography (SPECT) system, a magnetic resonance imaging (MM) system or an ultrasound device, and adding data from the third image in the virtual image.

For example, the third image may be an X-ray image, which may be acquired by receiving the image from an X-ray imaging system, by receiving the image from an intermediate device, which forwards the image, or by retrieving the image from a storage medium. The X-ray image may be a two-dimensional image or a three-dimensional model determined by a computed tomography (CT) system. The third image may be associated with a coordinate system of the X-ray imaging system, and the method may comprise transforming the third image based on the coordinate system of the X-ray imaging system and based on the image capturing position and orientation of the virtual image. Alternatively, the transformation based on the coordinate system of the X-ray imaging system and based on the image capturing position and orientation of the virtual image may have been performed, for example by the X-ray imaging system, before the third image is acquired. Hence, the method may comprise adding data from the third image or the transformed third image in the virtual image in accordance with the image capturing position and orientation of the virtual image.

Similarly, the third image may be a SPECT image, which may be acquired by receiving the image from a SPECT system, by receiving the image from an intermediate device, which forwards the image, or by retrieving the image from a storage medium. The SPECT image may be a two-dimensional image or a three-dimensional model determined by a tomographic reconstruction. The third image may be associated with a coordinate system of the SPECT system, and the method may comprise transforming the third image based on the coordinate system of the SPECT system and based on the image capturing position and orientation of the virtual image. Alternatively, the transformation based on the coordinate system of the SPECT system and based on the image capturing position and orientation of the virtual image may have been performed, for example by the SPECT system, before the third image is acquired. Hence, the method may comprise adding data from the third image or the transformed third image in the virtual image in accordance with the image capturing position and orientation of the virtual image.

Similarly, the third image may be an MRI image, which may be acquired by receiving the image from an Mill system, by receiving the image from an intermediate device, which forwards the image, or by retrieving the image from a storage medium. The Mill image may be a two- or three-dimensional image. The third image may be associated with a coordinate system of the Mill system, and the method may comprise transforming the third image based on the coordinate system of the MM system and based on the image capturing position and orientation of the virtual image. Alternatively, the transformation based on the coordinate system of the MM system and based on the image capturing position and orientation of the virtual image may have been performed, for example by the MM system, before the third image is acquired. Hence, the method may comprise adding data from the third image or the transformed third image in the virtual image in accordance with the image capturing position and orientation of the virtual image.

Furthermore, the third image may be an ultrasound image, which may be acquired by receiving the image from an ultrasound device, by receiving the image from an intermediate device, which forwards the image, or by retrieving the image from a storage medium. The ultrasound image may be a two- or three-dimensional image. The method may comprise determining a third position and orientation of the ultrasound device based on the sensor data. Furthermore, the method may comprise transforming the third image based on the third position and orientation of the ultrasound device and based on the image capturing position and orientation of the virtual image. Alternatively, the transformation based on third position and orientation of the ultrasound device and based on the image capturing position and orientation of the virtual image may have been performed before the third image is acquired, for example by the ultrasound device. Hence, the method may comprise adding data from the third image or the transformed third image in the virtual image in accordance with the image capturing position and orientation of the virtual image.

In another example, the determination of the second image is also based on a determination for one or more images if they depict an instrument to ensure that the determined second image does not depict an instrument.

Herein, an image is said to depict an instrument when the image depicts at least a part of the instrument.

Determining the second image may comprise, for example, retrieving a particular image from the sequence of historic images based on a measure for a difference between the first position and orientation of the endoscope and an image capturing position and orientation of the particular image. The second image may be determined based on the retrieved particular image and based on a determination if the particular image depicts an instrument to ensure that the second image does not show an instrument. For example, when the particular image does not depict an instrument, the second image may be equal to the particular image. On the other hand, when the particular image depicts an instrument, the position and orientation of the instrument at the image capturing time of the particular image may be different from the second position and orientation of the instrument determined based on the sensor data. Then, the particular image may be transformed based on the sequence of historic images to remove the visualization of the instrument from the particular image.

Alternatively, a three-dimensional model may be generated from the sequence of two-dimensional historic images, and the second image may be determined based on the three-dimensional model and the first position and orientation of the endoscope. The sequence of historic images may comprise images, which depict an instrument, and other images, which do not depict an instrument. It may be determined for one or more historic images from the sequence of historic images if they depict an instrument to ensure that parts of historic images, which depict an instrument, are not taken into account for generating the three-dimensional model, so that also the determined second image does not depict an instrument. Alternatively, before including an image in the sequence of historic images, it may be determined if the image shows an instrument to ensure that the sequence of historic images comprises only historic images, which do not show an instrument.

It is emphasized, however, that the invention as described above and in the following does not involve or in particular comprise or encompass an invasive step which would represent a substantial physical interference with the body of a patient requiring professional medical expertise to be carried out and entailing a substantial health risk even when carried out with the required professional care and expertise. In particular, the invention does not involve or in particular comprise or encompass any surgical or therapeutic activity. The invention is instead directed as applicable to any non-invasive medical application and merely relates to a data processing method. For this reason alone, no surgical or therapeutic activity and in particular no surgical or therapeutic step is necessitated or implied by carrying out the invention.

According to the present disclosure, also a data processing system is presented. The data processing system is configured to carry out the steps of any of the methods according to the present invention.

The data processing system may be connected to an endoscope. Furthermore, the data processing system may be connected to a tracking system, for example, a camera-based tracking system. The data processing system may further comprise a storage medium for storing the sequence of historic images in a database. The database may further comprise, for at least some of the historic images, image capturing positions and orientations, indicators of image capturing times, indicators indicating if an image is at least partly obscured, and/or indicators indicating if an image depicts an instrument. Furthermore, the data processing system may be connected to or may comprise one or more computer screens.

According to the present disclosure, also a computer program is presented, wherein the computer program comprises instructions to cause the data processing system as defined in the independent claims to execute any one of the methods according to the present invention when the computer program is run on the data processing system.

According to the present disclosure, also a computer-readable medium is presented, wherein the computer-readable medium stores the computer program as defined in the independent claims.

It shall be understood that the computer-implemented method for an image-assisted medical application, the data processing system configured to carry out the steps of the method, the computer program for causing the data processing system to execute the method, and the computer readable medium having stored such computer program have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings:

FIG. 1 shows basic steps of an example of a computer-implemented method for an image-assisted medical application.

FIG. 2 shows schematically and exemplarily a non-obscured endoscopic image (FIG. 2*a*) and a virtual computer-generated image (FIG. 2*b*).

FIG. 3 shows schematically and exemplarily an obscured endoscopic image (FIG. 3*a*) and a virtual image (FIG. 3*b*) generated by the computer-implemented method as illustrated by FIG. 1.

FIG. 4 shows schematically and exemplarily an embodiment of a data processing system for carrying out the computer-implemented method for an image-assisted medical application.

DETAILED DESCRIPTION OF EMBODIMENTS

FIG. 1 shows basic steps of an example of a computer-implemented method for an image-assisted medical application. The method comprises the following steps:

In a first step S1, a first image of at least one body part of a patient is acquired, the first image being captured with an endoscope and being associated with sensor data, the sensor data being indicative of a first position and orientation of the endoscope. The first image may be received from the endoscope or from an intermediate device, which forwards the first image. Alternatively, the first image may be retrieved from a storage medium.

The sensor data may have been recorded by a tracking system such as a camera-based tracking system. The sensor data may be received from the tracking system or from an intermediate device, which forwards the sensor data. Alternatively, the sensor data may be retrieved from a storage medium. The camera-based tracking system may comprise one or more cameras, which capture images from one or more positions and orientations. Hence, the sensor data may comprise one or more camera images. At least a proximal end of the endoscope may be visible in one or more of these images. The first position and orientation of the endoscope may be determined based on this visualization of the proximal end of the endoscope in one or more camera images. The endoscope is preferably a rigid endoscope so that the position and orientation of the camera at the distal end of the endoscope can be inferred from the position and orientation of the visible proximal end of the endoscope. The first position and orientation of the endoscope may be defined as the position and orientation of the endoscopic camera. Preferably, the sensor data is recorded by the tracking system at approximately the same time when the endoscope captures the first image. Hence, the first position and orientation of the endoscope may be an estimate of the image capturing position and orientation of the first image.

In a second step S2, it is detected if the first image is at least partly obscured by obscuring matter, wherein the obscuring matter is a leaking body fluid, debris or smoke from ablation. The obscuring matter may obscure a part of the first image, so that the first image may not show for example an instrument and/or a region-of-interest. Thus, due to the obscuring matter, it may be difficult or impossible to securely navigate the instrument towards the region-of-interest based on the first image.

In a third step S3, upon detecting that the first image is at least partly obscured, a second image is determined based on a sequence of historic images and based on the first position and orientation of the endoscope, wherein the historic images of the sequence of historic images each have image capturing times earlier than the first image. When it is detected that the first image is at least partly obscured, the first position and orientation of the endoscope may be determined based on the sensor data, and the second image may be determined based on the sequence of historic images and based on the first position and orientation of the endoscope. The sequence of historic images may comprise endoscopic images, which have been captured by the endoscope before capturing the first image.

In a fourth step S4, a virtual image of the at least one body part is generated based on the determined second image. The virtual image may be equal to the second image. However, the generation of the virtual image may also comprise various transformations of the second image. For example, the second image may be transformed to adjust its associated image capturing position and orientation. Furthermore, the second image may be augmented with a rendering of an instrument. In addition, the second image may be augmented with image data from an X-ray imaging system, a magnetic resonance imaging (Mill) system, a single-photon emission computerized tomography (SPECT) system or an ultrasound device.

Even when the first image is obscured by obscuring matter, the virtual image may provide a virtual endoscopic view, which is not obscured by such matter.

Note that step S3 is performed upon detecting that the first image is obscured by obscuring matter. Additionally or alternatively, the determination of the second image and the generation of the virtual image may be performed upon receiving a request from a user to generate the virtual image. Furthermore, in another method, the second image may be determined and the virtual image may be generated even if the first image is not obscured by obscuring matter and even if the generation of the virtual image is not requested. When the first image is not obscured, the virtual image may still be generated to assess the reliability/accuracy of the generated virtual image.

FIG. 2 shows schematically and exemplarily a non-obscured endoscopic image 200 and a virtual image 210. The non-obscured endoscopic image 200 comprises a presentation of an instrument 201 and a presentation of a lesion 202, wherein the lesion may require treatment. The non-obscured image 200 may be associated with sensor data, which may allow determining the first position and orientation of the endoscope as an estimate for the image capturing position and orientation of the image 200.

The virtual image 210 may have been generated based on a second image, wherein the second image may have been determined based on a sequence of historic images and based on the first position and orientation of the endoscope. The historic images of the sequence of historic images may each have image capturing times earlier than the image 200. The virtual image 210 shows a visualization of the instrument 211 and a visualization of the lesion 212. Since the image 200 is not obscured by obscuring matter, the virtual image 210 may be essentially identical with the image 200.

FIG. 3 shows schematically and exemplarily an obscured endoscopic image 300 and a virtual image 310. The scenario of FIG. 3 differs from the scenario of FIG. 2 in that the image 300 is partly obscured by obscuring matter 303, which may be bleeding. The image 300 further comprises a presentation of an instrument 301. The obscured image 300 may be associated with sensor data, which may allow determining the first position and orientation of the endoscope as an estimate of the image capturing position and orientation of the image 300.

FIG. 4 shows schematically and exemplarily an embodiment of a data processing system 400 for carrying out the computer-implemented method 100 for an image-assisted medical application. The data processing system may comprise a processor 401 and a storage medium 402. The data processing system may be connected to an endoscope 404 and may be configured for acquiring a first image of at least one body part of a patient, the first image being captured with the endoscope. Furthermore, the data processing system may be connected to a tracking system 405, for example a camera-based tracking system. The data processing system may be configured to acquire sensor data, the sensor data being recorded by the tracking system. The data processing system may be configured to determine the first position and orientation of the endoscope based on the sensor data. The first position and orientation of the endoscope may be an estimate of the image capturing position and orientation of the first image. Furthermore, the data processing system may be configured to detect if the first image is at least partly obscured by obscuring matter, wherein the obscuring matter is a leaking body fluid, debris or smoke from ablation. In addition, the data processing system may be configured to determine, upon detecting that the first image is at least partly obscured, a second image based on the first position and orientation of the endoscope and based on a sequence of historic images 403, which may be stored on the storage medium of the data processing system. Alternatively, the sequence of historic images may be stored on an external storage medium or on a server connected to the data processing system. Moreover, the data processing system may be configured for generating a virtual image of the at least one body part based on the determined second image.

The data processing system may be connected to an X-ray imaging system 407, and the data processing system may be configured to acquire an X-ray image being captured with the X-ray imaging system and to add data from the X-ray image in the virtual image. Additionally or alternatively, the data processing system may be connected to a CT system, a SPECT system, an Mill system or an ultrasound device, and the data processing system may be configured to add image data from such a system or device in the virtual image (not shown in the figure).

The data processing system may also be connected to a display 406, and the data processing system may be configured to display the first and virtual images next to each other by means of the display.

It has to be noted that embodiments of the invention are described with reference to different subject matters. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A computer-implemented method for an image-assisted medical application, the method comprising:
   acquiring, by an endoscope, a first image of at least one body part of a patient, the first image associated with sensor data indicative of a first position of the endoscope and a first orientation of the endoscope;
   detecting if the first image includes obscuring matter that obscures at least a portion of the at least one body part in the first image, the obscuring matter comprising at least one of a leaking body fluid, debris, or smoke from ablation;
   determining, in response to detecting that the first image includes obscuring matter, a second image based on a sequence of historic images with image capturing times earlier than the first image, wherein the second image is determined from the sequence of historic images based on a difference between (a) the first position of the endoscope and the first orientation of the endoscope and (b) an image capturing position and orientation of the second image; and
   generating a virtual image of the at least one body part based on the determined second image.

2. The method of claim 1, wherein the sensor data is also indicative of a position of an instrument and an orientation of the instrument, and wherein the method further comprises:
   determining a second position of the instrument and a second orientation of the instrument based on the sensor data; and
   augmenting the virtual image with a rendering of the instrument in accordance with the second position of the instrument and the second orientation of the instrument and in accordance with an image capturing position and orientation of the virtual image.

3. The method of claim 1, wherein determining the second image is based on a determination that one or more of the historical images fail to include an image of the obscuring matter to ensure that the second image does not include an image of the obscuring matter.

4. The method of claim 1, wherein generating the virtual image comprises:
   transforming the second image based on a motion technique, wherein the virtual image corresponds to an image capturing position and orientation corresponding to the first position of the endoscope and the first orientation of the endoscope.

5. The method of claim 1, further comprising:
   displaying an indicator of the difference between (a) the first position of the endoscope and the first orientation of the endoscope and (b) the image capturing position and orientation of the second image.

6. The method) of claim 1, further comprising:
   displaying the first image from the endoscope next to the virtual image.

7. The method of claim 1, wherein the historic images of the sequence of historic images are endoscopic images.

8. The method of claim 1, wherein detecting if the first image includes an image of the obscuring matter comprises:
   detecting if the first image includes an image of a bleeding based on determining at least one of a size of a red section in the first image and a contrast in at least a part of the first image.

9. The method of claim 1, further comprising at least one of:
   determining a position of an origin of the obscuring matter based on the sequence of historic images; and
   indicating the position of the origin of the obscuring matter in the virtual image.

10. The method of claim 1, wherein at least one of: the sensor data is received from a camera-based tracking system; and
   the first position and the first orientation of the endoscope is determined based on a marker plate attached to the endoscope.

11. The method of claim 1, further comprising:
   acquiring a third image captured with an X-ray imaging system, a computed tomography (CT) system, a single-photon emission computerized tomography (SPECT) system, a magnetic resonance imaging (MRI) system, or an ultrasound device; and
   adding data from the third image in the virtual image.

12. A non-transitory computer-readable medium having stored a computer program comprising instructions, which, when executed by a processor, cause the processor to:
   receive a first image of at least one body part of a patient captured by an endoscope, the first image associated with sensor data indicative of a first position of the endoscope and a first orientation of the endoscope;
   detect if the first image includes obscuring matter that obscures at least a portion of the at least one body part in the first image, the obscuring matter comprising at least one of a leaking body fluid, debris, or smoke from ablation;
   in response to the detection that the first image includes the obscuring matter, determine a second image based on a sequence of historic images with image capturing times earlier than the first image, wherein the second image is determined from the sequence of historic images based on a difference between (a) the first position of the endoscope and the first orientation of the endoscope and (b) an image capturing position and orientation of the second image; and
   generate a virtual image of the at least one body part based on the determined second image.

13. The non-transitory computer-readable medium of claim 12, wherein, when executed by the processor, the instructions further cause the processor to:
   determine the second image based on a determination that one or more of the historical images fail to include an image of the obscuring matter to ensure that the second image does not include an image of the obscuring matter.

14. A system for an image-assisted medical application, the system comprising:
   an endoscope configured to capture a first image of at least one body part of a patient, the first image associated with sensor data indicative of a first position of the endoscope and a first orientation of the endoscope; and
   at least one processor configured to:
      receive the first image of the at least one body part of the patient captured by the endoscope, detect if the first image includes obscuring matter that obscures at least a portion of the at least one body part in the first image, the obscuring matter comprising at least one of a leaking body fluid, debris, or smoke from ablation, in response to the detection that the first image includes the obscuring matter, determine a second image based on a sequence of historic images with image capturing times earlier than the first image, wherein the second image is determined from the sequence of historic images based on a difference between (a) the first position of the endoscope and the first orientation of the endoscope and (b) an image capturing position and orientation of the second image, and generate a virtual image of the at least one body part based on the determined second image.

15. The system of claim 14, wherein the at least one processor is further configured to:

determine the second image based on a determination that one or more of the historical images fail to include an image of the obscuring matter to ensure that the second image does not include an image of the obscuring matter.

* * * * *